United States Patent [19]

Bermudez

[11] Patent Number: 5,096,573
[45] Date of Patent: Mar. 17, 1992

[54] BLOOD AND FLUID SEPARATOR APPARATUS

[76] Inventor: Wilfred Bermudez, c-15 Rio Cialitos Ave., Rio Hondo Bayamon, P.R. 00619

[21] Appl. No.: 673,010

[22] Filed: Mar. 21, 1991

[51] Int. Cl.$^5$ .............................................. B01D 21/26
[52] U.S. Cl. .................................... 210/85; 210/198.1; 210/207; 210/361; 210/380.1; 210/514; 422/64; 422/72; 422/73; 422/102; 494/17; 494/20; 494/32; 494/33
[58] Field of Search ................... 210/85, 198.1, 360.1, 210/361, 380.1, 205, 207, 513, 514; 422/102, 64, 72, 73; 494/17, 20, 31, 32, 33

[56] References Cited

U.S. PATENT DOCUMENTS

| 1,001,611 | 8/1911 | Boekel | 494/20 |
| 1,769,889 | 7/1930 | McClaran et al. | 494/20 |
| 3,603,156 | 9/1971 | Konkol | 422/102 |
| 4,397,897 | 8/1983 | Schulke | 422/102 |
| 4,886,486 | 12/1989 | Grimm et al. | 494/20 |

Primary Examiner—W. Gary Jones
Attorney, Agent, or Firm—Leon Gilden

[57] ABSTRACT

An apparatus wherein a centrifuge organization includes a mounting ring, and includes a plurality of pairs of stirrups, each securing therewithin an associated container. Each container includes a color-coded lid and anhydrous gel cylindrical floor and an annular wall, including a coating of silicone in a powdered or gel form. Vacuum porting is provided through each lid of each container in cooperation with an intake conduit for directing blood and associated fluid into the container.

3 Claims, 5 Drawing Sheets

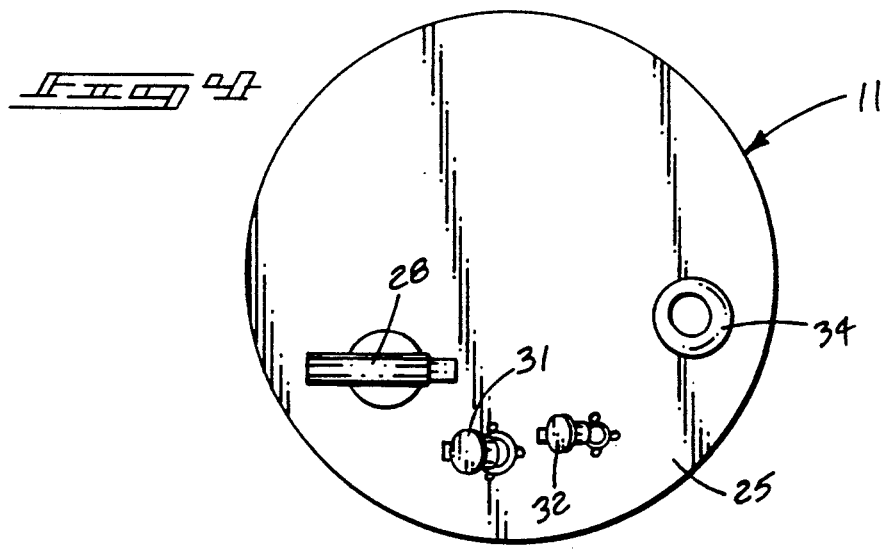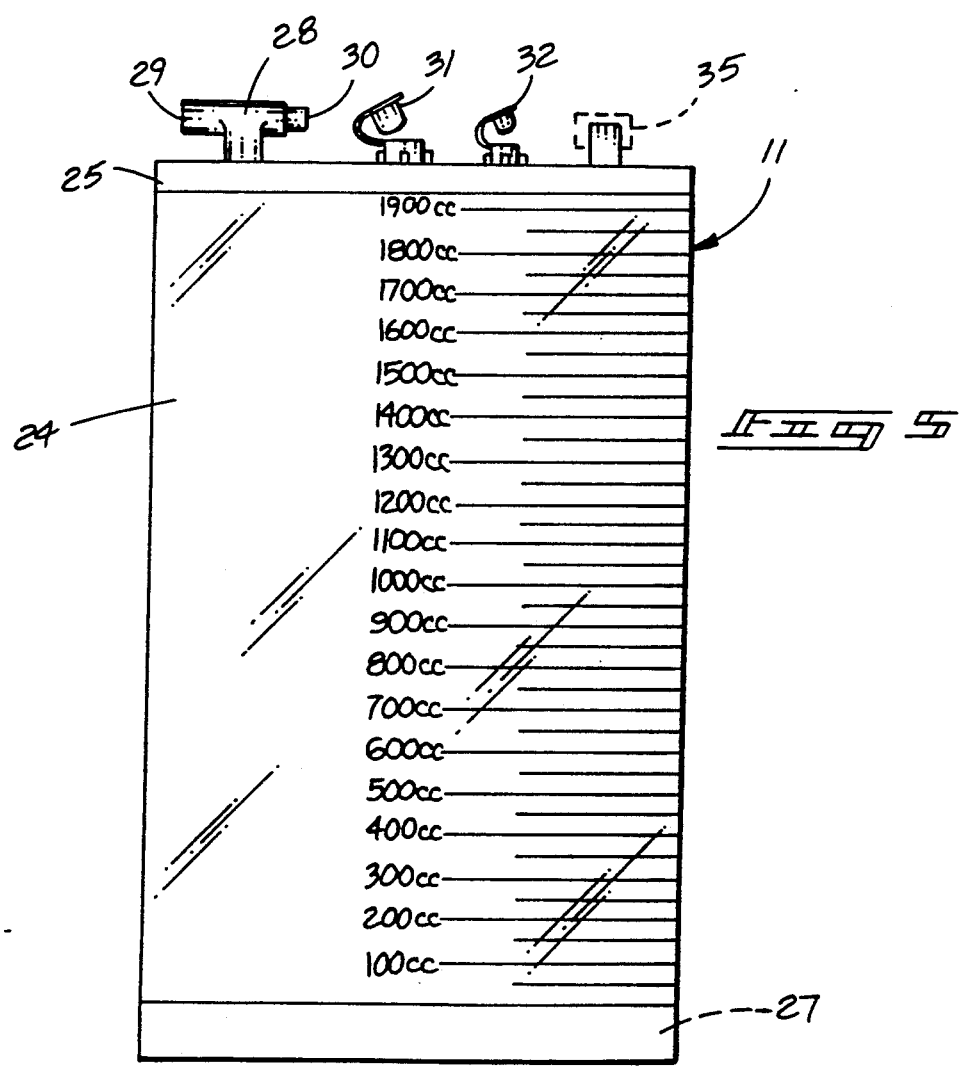

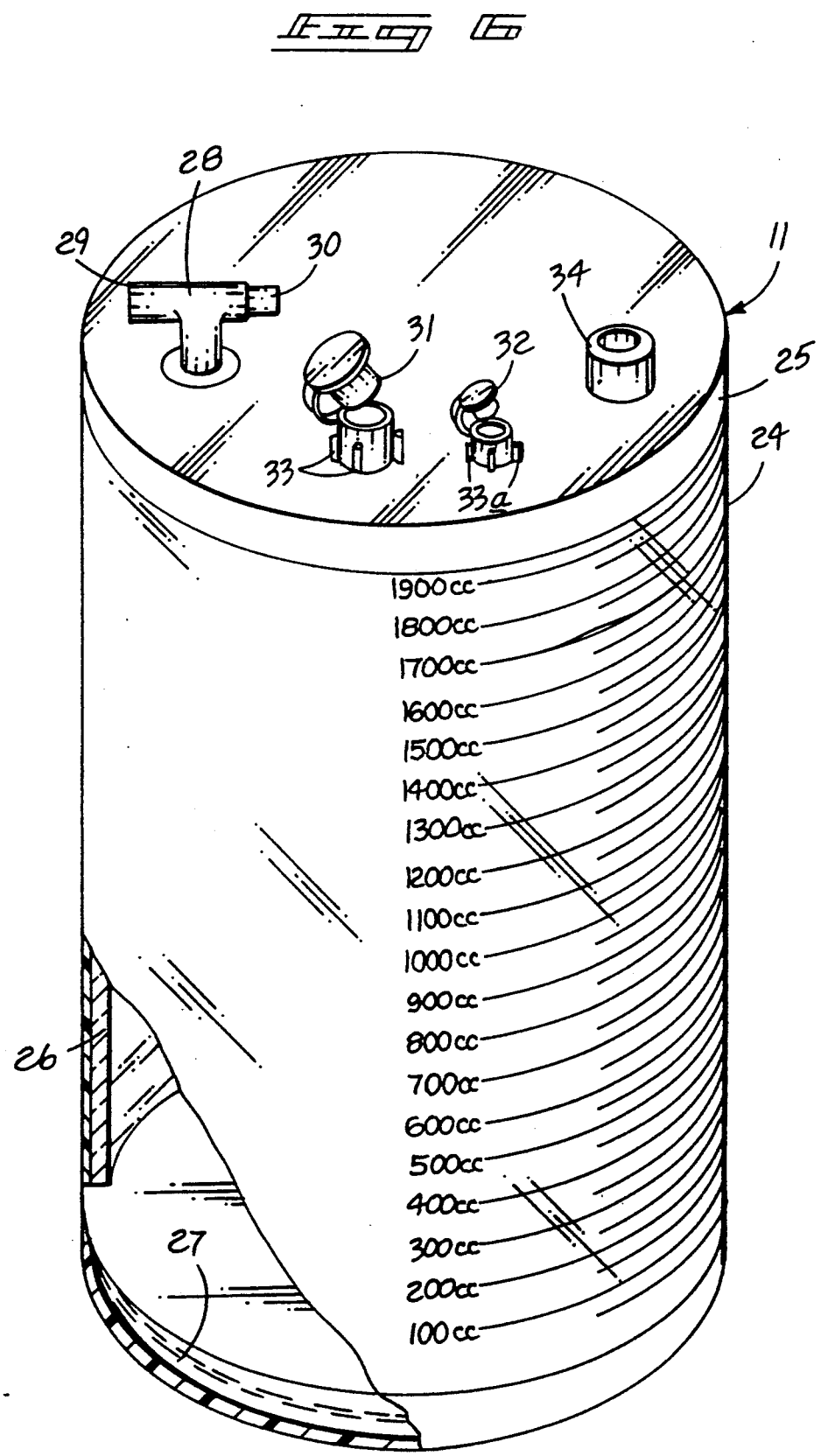

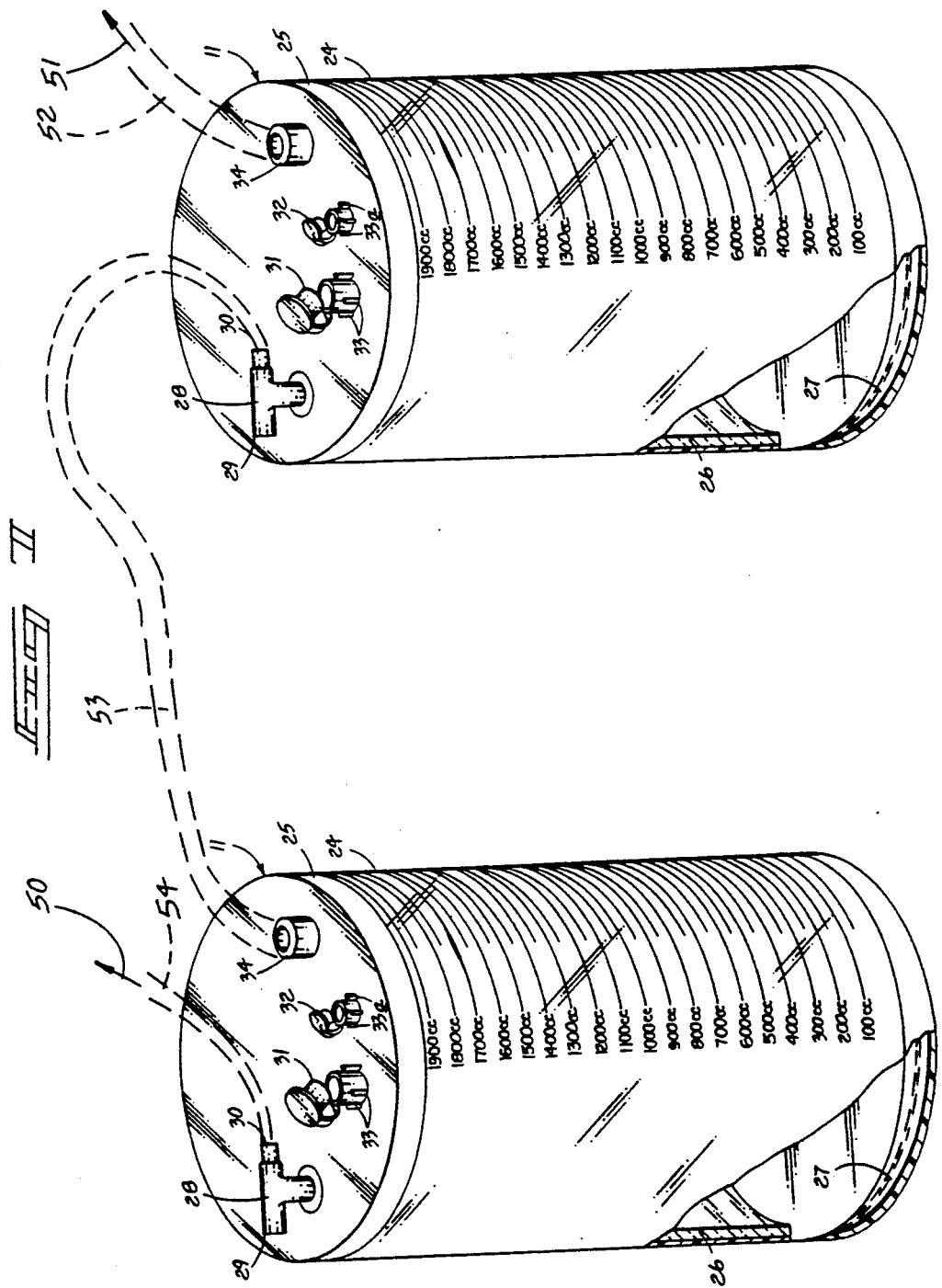

BLOOD AND FLUID SEPARATOR APPARATUS

BACKGROUND OF THE INVENTION

1. Field of the Invention

The field of invention relates to analyzing apparatus, and more particularly pertains to a new and improved blood and fluid separator apparatus wherein the same permits separating of blood from associated fluid such as utilized during surgery to provide evidence of blood loss effected during surgery.

2. Description of the Prior Art

Surgical procedures require accounting for blood utilized and lost by a patient during a surgical procedure. Blood is frequently in a mixture with other fluids, such as irrigations fluids and the like, utilized in a medical surgical procedure, wherein the instant invention provides an organization to separate such blood and fluid to provide quantitative evidence of blood removed from a patient during a surgical procedure.

Prior art medical analysis devices are frequently utilized and are exemplified by U.S. Pat. No. 4,756,883 to Romanauskas wherein a centrifugal analysis device is arranged providing a plurality of cells for mounting various centrifugal vials therewithin.

U.S. Pat. No. 4,708.940 to Yoshida; U.S. Pat. No. 4,865,810 to Simon; and U.S. Pat. No. 4,812,294 to Combs are further examples of centrifuge devices utilized in the prior art.

As such, it may be appreciated that there continues to be a need for a new and improved blood and fluid separator apparatus as set forth by the instant invention which addresses both the problems of ease of use as well as effectiveness and in this respect, the present invention substantially fulfills this need.

SUMMARY OF THE INVENTION

In view of the foregoing disadvantages inherent in the known types of centrifuge apparatus now present in the prior art, the present invention provides a blood and fluid separator apparatus wherein the same is arranged to enhance and expedite removal of fluid relative to blood lost by a patient during surgical procedures to quantitatively account for such blood loss. As such, the general purpose of the present invention, which will be described subsequently in greater detail, is to provide a new and improved blood and fluid separator apparatus which has all the advantages of the prior art medial analysis apparatus and none of the disadvantages.

To attain this, the present invention provides an apparatus wherein a centrifuge organization includes a mounting ring, and includes a plurality of pairs of stirrups, each securing therewithin an associated container. Each container includes a color-coded lid and anyhdrous gel cylindrical floor and an annular wall, including a coating of silicone in a powdered or gel form. Vacuum porting is provided through each lid of each container in cooperation with an intake conduit for directing blood and associated fluid into the container.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved blood and fluid separator apparatus which has all the advantages of the prior art centrifuge apparatus and none of the disadvantages.

It is another object of the present invention to provide a new and improved blood and fluid separator apparatus which may be easily and efficiently manufactured and marketed.

It is a further object of the present invention to provide a new and improved blood and fluid separator apparatus which is of a durable and reliable construction.

An even further object of the present invention is to provide a new and improved blood and fluid separator apparatus which is susceptible of a low cost of manufacture with regard to both materials and labor, and which accordingly is then susceptible of low prices of sale to the consuming public, thereby making such blood and fluid separator apparatus economically available to the buying public.

Still yet another object of the present invention is to provide a new and improved blood and fluid separator apparatus which provides in the apparatuses and methods of the prior art some of the advantages thereof, while simultaneously overcoming some of the disadvantages normally associated therewith.

Still another object of the present invention is to provide a new and improved blood and fluid separator apparatus wherein the same utilizes a container mounting a plurality of coatings therewithin to enhance removal of fluid relative to blood during a centrifuge procedure.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an orthographic top view of the container utilized by the instant invention.

FIG. 5 is an orthographic side view, taken in elevation, of the container utilized by the instant invention.

FIG. 6 is an isometric illustration, partially in section, of the container utilized by the instant invention.

FIG. 7 is an isometric illustration of the instant invention in use in tandem, with a primary container in use with a secondary container.

DESCRIPTION OF THE PREFERRED EMBODIMENT

Figure 1:
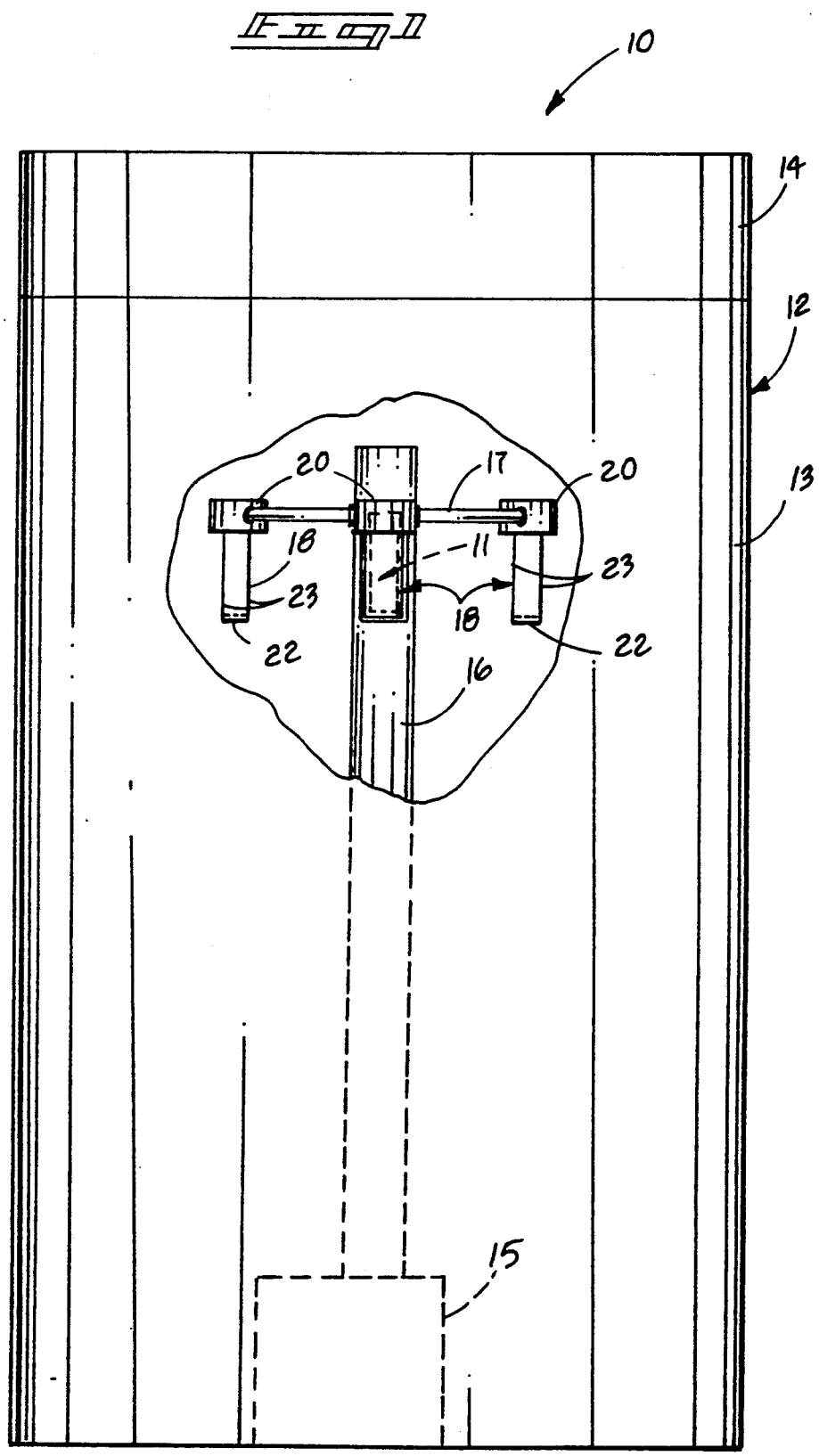
FIG. 1 is an orthographic side view of the instant invention, taken in elevation.

With reference now to the drawings, and in particular to FIGS. 1 to 7 thereof, a new and improved blood and fluid separator apparatus embodying the principles and concepts of the present invention and generally designated by the reference numeral 10 will be described.

More specifically, the blood and fluid separator apparatus 10 of the instant invention essentially comprises a centrifuge assembly 12 mounting a plurality of containers 11 therewithin for effecting a centrifuge procedure. The centrifuge assembly 12 includes an elongate, coaxially aligned housing 13 mounting a removable lid, wherein the housing includes a drive motor 15. The drive motor is configured to effect rotation of the associated rotor 16 at substantially 6,000 rpm. The housing may utilize wheels at the bottom surface thereof for transport of the housing (not shown). The motor is provided with an organization to effect a braking system to effect selective braking of the motor when required. The housing and lid 13 and 14 respectively are typically formed of stainless steel, and wherein the motor may be optionally provided with a brush wear indicator system (not shown) available in the prior art to effect indication of motor reliability, as well as a timer system to permit an individual to direct rotation of the rotor 16 for a predetermined time interval.

Figure 2:
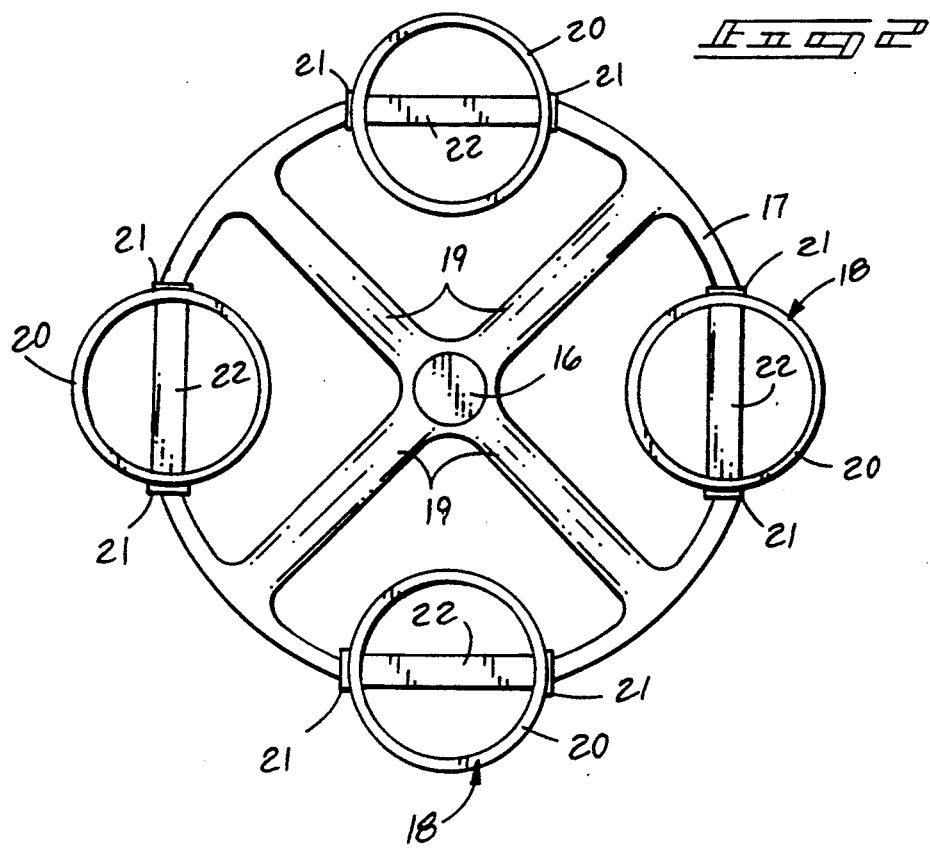
FIG. 2 is an orthographic top view of the mounting ring and associated stirrups for supporting the containers utilized by the centrifuge assembly.
Figure 3:
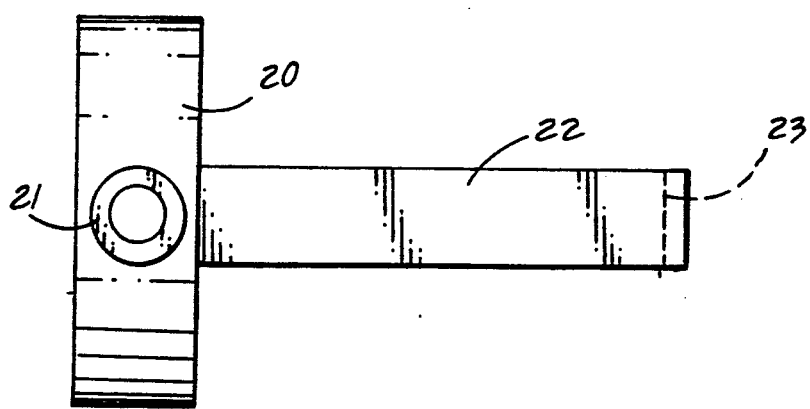
FIG. 3 is an orthographic side view of a stirrup assembly as utilized by the instant invention.

The rotor 16 orthogonally mounts a torroidal mounting ring 17 adjacent an upper terminal end thereof in a fixed relationship. The ring 17 includes plural pairs of stirrup assemblies 18 that are diametrically opposed relative to one another about the mounting ring 17. The mounting ring 17 includes a plurality of radial mounting legs 19 securing the ring 17 to the rotor 16, as illustrated in FIG. 2 for example. Each stirrup assembly 18 includes a cylindrical upper band 20. The upper band 20 includes a plurality of diametrically opposed cylindrical bearings 21 directed through side walls of the upper band 20 for securement in a rotational manner to the ring 17 to permit pivoting of the stirrup relative to the ring during rotation of the ring in a centrifuge procedure. Each cylindrical upper band 20 includes a "U" shaped underlying support defined by a bottom strap 22 and parallel side straps 23, wherein the side straps 23 are fixedly mounted at their upper terminal ends to diametrically opposed portions of the upper band in alignment and underlying each bearing 21. This permits free swinging of each stirrup assembly 18 relative to the axial center of the rotating rotor 16. The parallel side straps 23 are spaced apart a predetermined spacing.

Each container 11 is defined by a cylindrical housing 24 defined by a diameter substantially equal to the predetermined spacing. A removable lid 25 is mounted upon the cylindrical housing 24, wherein the removable lid 25 is preferably color coded, such as red or green, wherein red would typically indicate special handling and destruction of the lid such as in the use of contaminated blood, wherein green may permit disposing in a conventional manner of the contents of the container or permit storage thereof.

The cylindrical housing 24 of each container 11 includes a silica coating 26 laminated and adhered to an interior surface of the cylindrical wall of each container. The silica coating triggers formation of fibrin for enhanced clotting of the blood and its removal from other fluids, such as irrigation fluid directed within the container. The floor of the container of a planar construction and orthogonally oriented relative to an axis defined by the container includes an anhydrous cylindrical gel base 27 for enhanced removal of fluid from the blood, wherein the base is formed of a polymer not to be effected by irradiation or sterilization.

The lid 25 includes a "T" shaped vacuum port 28 to secure a vacuum thereto to direct fluid therewithin through an associated intake port 34. The vacuum port 28 may include a first and second diameter exhaust port 29 and 30 defined by respective first and second diameters. A respective first and second drain plug 31 and 32 defined by the respective first and second diameters are mounted within respective first and second positioning pins 33 and 33a, each securing a cylindrical hoop structure of each drain plug for overlying each respective first and second diameter port 29 and 30. The intake port 34 is provided with a cap 35 for containment of all fluid within the container 11 during its centrifuge, transport, and storage.

FIG. 7 illustrates the use of the organization, wherein a primary container 11a is utilized with a secondary container 11. The primary container 11a utilizes a first conduit 51 directed to a patient forming a suction tube for withdrawing fluids from such a patient. A second conduit 53 is directed from the port 30 to the intake port 34. The use of a third conduit 54 is mounted to the second port 30 of the secondary container 11 directed to a suction source. The first port 29 of the primary and secondary containers 11a and 11 are sealed to create internal negative hydrostatic pressure within the containers. In this manner, the third conduit is not contaminated with fluid from the first conduit and provides an overflow container for use in the organization.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A blood and fluid separator apparatus comprising, in combination,
    a centrifuge assembly, the centrifuge assembly including an elongate, coaxially aligned housing, the housing including a drive motor mounted therewithin, wherein the drive motor includes a rotor directed coaxially of the housing, with the rotor arranged for rotation by the drive motor, and
    a torroidal mounting ring mounted adjacent an upper terminal end of the rotor, the mounting ring including plural pairs of diametrically opposed stirrup assemblies, each of the stirrup assemblies including a cylindrical upper band, each cylindrical upper band including a plurality of diametrically opposed cylindrical bearing, wherein each cylindrical bearing is mounted within the mounting ring, and each stirrup assembly of the plurality of stirrup assemblies includes a "U" shaped support mounted fixedly to and underlying the cylindrical upper band, wherein the "U" shaped support includes a bottom strap and parallel side straps spaced apart a predetermined spacing, wherein each parallel side strap of the parallel side straps is fixedly mounted to a lower terminal end of the cylindrical band underlying an associated bearing, and
    a container mounted within each stirrup assembly of the plurality of stirrup assemblies, and
    wherein each container includes a cylindrical housing defined by a diameter substantially equal to the predetermined spacing, and
    wherein each cylindrical housing includes a removable lid selectively securable to an upper terminal end of the cylindrical housing, wherein the removable lid is color coded for directing selective disposal or storage of the container, and
    wherein each cylindrical housing includes a planar floor orthogonally oriented relative to an axis defined by each cylindrical housing, the planar floor including an anhydrous cylindrical gel base secured to the floor, and the cylindrical housing further including a cylindrical wall structure, wherein the cylindrical wall structure includes a silica coating coextensively laminated to the cylindrical wall interior surface, wherein the silica coating enhances fibrin formation for enhanced blood clotting for separation of blood relative to irrigation fluid directed within the container.

2. An apparatus as set forth in claim 1 wherein each removable lid of each container includes a "T" shaped vacuum port, the "T" shaped vacuum port including a first port of a first diameter and a second port of a second diameter for permitting selective coupling of vacuum sources of varying diameter connections, and further including a first diameter plug removably mounted on the lid for securement within the first diameter port, and a second diameter plug removably mounted on the lid for positioning within the second diameter port, and each plug includes a cylindrical collar, and each cylindrical collar includes a plurality of positioning pins fixedly mounted to the lid, and an intake port directed through the lid for directing fluid into the lid, wherein the intake port includes a cap removably mounted overlying the intake port for sealing of fluid within the container.

3. An apparatus as set forth in claim 2 including a secondary container, and the secondary container includes the first port capped and the secondary container includes a removable lid, including a "T" shaped vacuum port, wherein the "T" shaped vacuum port includes a first port capped, a second port of the "T" shaped vacuum port of the secondary container includes a third conduit for connection to a suction source, and an intake port mounted within the removable lid of the secondary container includes a second conduit, with the second conduit further mounted to the second port of the container, and the container including a first conduit mounted to the intake port and for connection to a patient for receiving bodily fluids from the patient.

* * * * *